(12) United States Patent
Choi et al.

(10) Patent No.: US 8,114,408 B2
(45) Date of Patent: Feb. 14, 2012

(54) PEPTIDE FRAGMENTS REACTING SPECIFICALLY WITH ANTIBODIES AGAINST HIGHLY PATHOGENIC NEWCASTLE DISEASE VIRUS AND USES THEREOF

(75) Inventors: Kang Seuk Choi, Seoul (KR); Eun Kyoung Lee, Seoul (KR); Woo-Jin Jeon, Anyang-si (KR); Eun-Im Yoon, Suwon-si (KR); Jun-Hun Kwon, Uiwang-si (KR)

(73) Assignee: Republic of Korea (Management: Ministry of Agriculture and Forestry, National Veterinary Research), Anyang-si (KR)

( * ) Notice: Subject to any disclaimer, the term of this patent is extended or adjusted under 35 U.S.C. 154(b) by 426 days.

(21) Appl. No.: 12/292,856

(22) Filed: Nov. 26, 2008

(65) Prior Publication Data
US 2010/0261206 A1   Oct. 14, 2010

(30) Foreign Application Priority Data

Nov. 30, 2007   (KR) .................. 10-2007-0123380

(51) Int. Cl.
| | |
|---|---|
| *A61K 39/12* | (2006.01) |
| *A61K 39/00* | (2006.01) |
| *A61K 39/17* | (2006.01) |
| *C12Q 1/70* | (2006.01) |
| *G01N 33/544* | (2006.01) |
| *C07K 16/00* | (2006.01) |

(52) U.S. Cl. ............... 424/186.1; 424/214.1; 424/178.1; 435/5; 435/7.1; 436/535; 530/328; 530/387.1

(58) Field of Classification Search ................. None
See application file for complete search history.

(56) References Cited

U.S. PATENT DOCUMENTS
2004/0235134 A1 * 11/2004 Peeters et al. .............. 435/235.1

FOREIGN PATENT DOCUMENTS
CN       1928117    *  3/2007

OTHER PUBLICATIONS

Umino et al., Monoclonal antibodies to three structural proteins of Newcastle disease virus: biological characterization with particular reference to the conformational change of envelope glycoproteins associated with proteolytic cleavage, 1990, Journal of General Virology, vol. 71, pp. 1189-1197.*

* cited by examiner

*Primary Examiner* — Benjamin P Blumel
(74) *Attorney, Agent, or Firm* — Sughrue Mion, PLLC

(57) ABSTRACT

We disclose synthetic peptide fragments comprising amino acid sequences of specific antigen sites of pathogenic Newcastle disease virus in birds, and more particularly synthetic peptide fragments that comprise polybasic amino acid sequences at the cleavage site of the F protein of pathogenic Newcastle disease virus and that induce humoral immune responses in hosts while reacting only with antibodies to pathogenic Newcastle disease virus and are useful to differentiate infected individuals from vaccinated individuals.

14 Claims, 4 Drawing Sheets

FIGURE 4

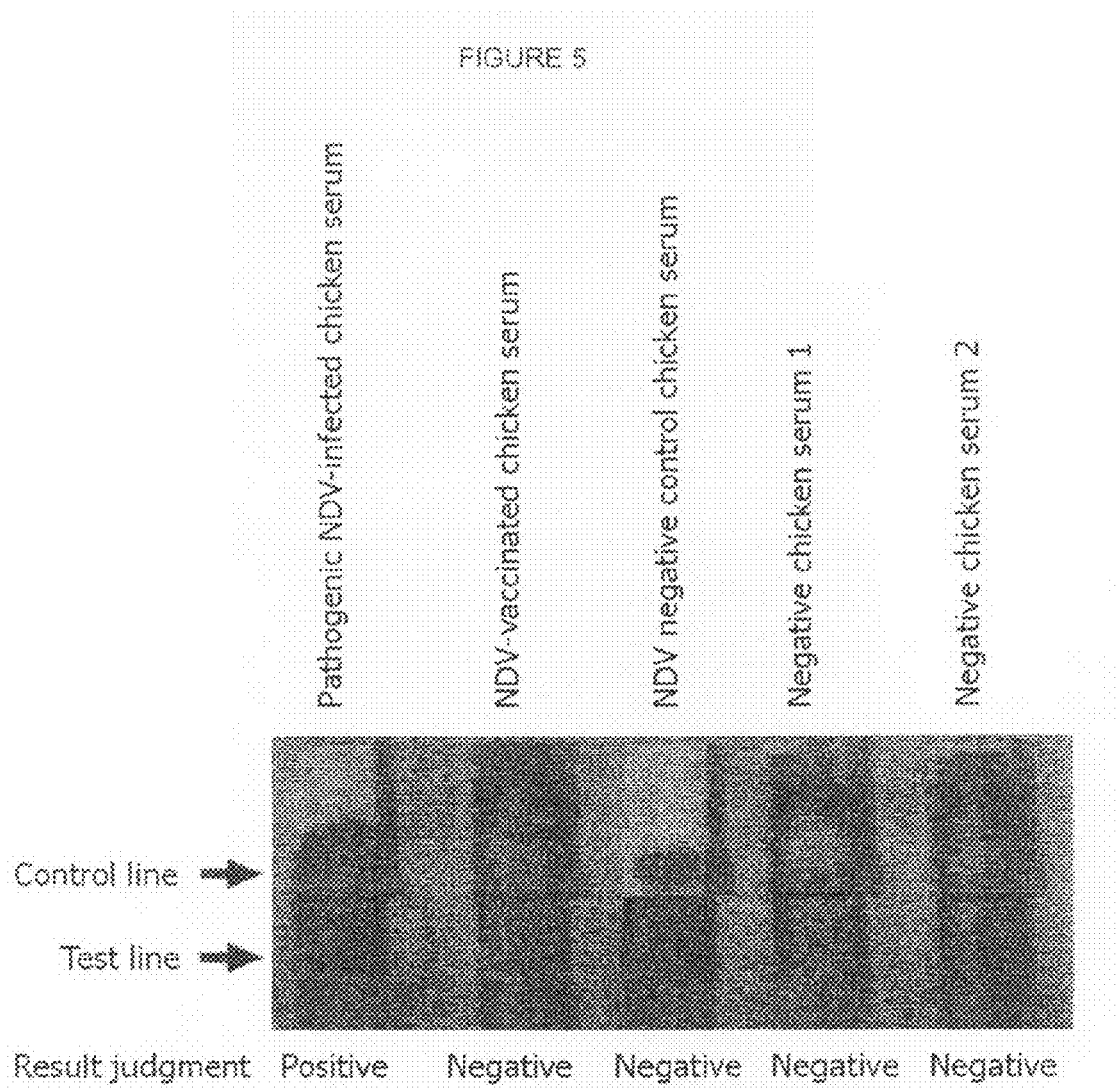

PEPTIDE FRAGMENTS REACTING SPECIFICALLY WITH ANTIBODIES AGAINST HIGHLY PATHOGENIC NEWCASTLE DISEASE VIRUS AND USES THEREOF

This application claims priority benefit of KR 10-2007-0123380, filed Nov. 30, 2007; the entire contents of which is hereby incorporated by reference.

FIELD OF THE INVENTION

The present invention relates to synthetic peptide fragments comprising amino acid sequences of specific antigen sites of pathogenic Newcastle disease virus in birds, and more particularly to novel synthetic peptide fragments that comprise polybasic amino acid sequences at the cleavage site of the F protein of pathogenic Newcastle disease virus and that induce humoral immune responses in hosts while reacting only with antibodies to pathogenic Newcastle disease virus and are useful to differentiate infected individuals from vaccinated individuals.

BACKGROUND OF THE INVENTION

Newcastle disease is a highly contagious' disease of poultry caused by Newcastle disease virus having an intracerebral pathogenicity index (ICPI) of 0.7 or more in chicken. In a case of unvaccinated chickens, chickens may show up to 100% mortality within 2 weeks. Chickens infected with Newcastle disease show clinical symptoms including depression, respiratory symptoms, neurologic symptoms and severe diarrhea.

Newcastle disease occurs in Asia, Africa, Europe, etc. and results in enormous economic losses in the poultry industry. In Korea, the first outbreak of Newcastle disease was recognized in the 1920s, and Newcastle disease virus was isolated for the first time in 1949. Newcastle disease has not yet been eradicated in Korea and the economic impact is enormous. In areas including Asia (including Korea) and Africa in which Newcastle disease is enzootic, vaccination policy has been implemented for protection of chickens against Newcastle disease. Currently, Newcastle disease vaccines are formulated using Newcastle disease virus having an intracerebral pathogenicity index of less than 0.4 (hereinafter referred to non-pathogenic virus) in the form of either live vaccines or inactivated killed vaccines.

Taxonomically, Newcastle virus is an RNA virus belonging to the family Paramyxoviridae, and the viral genome of an about 15.2 K nucleotide encodes at least 6 structural proteins, namely NP, P, M, F, HN and L. Among them, the F protein is a structural protein constituting the envelope of Newcastle disease virus along with the HN protein and induces a virus-neutralizing antibody in a host and plays an important role in the defense of a host against disease.

The mechanism of virus replication in susceptible host cells is as follows. The HN protein of the envelope of Newcastle disease virus attaches to the host cell membrane, and then the fusion between the viral envelope and the host cell membrane occurs, while a genome-containing nucleocapsid in the virions is introduced into the host cells. Then, the viral genome replicates genomic RNA using the metabolic system of the host cells and produces viral structural proteins, and thus the proteins are assembled into virion in the cells. Then, the viral particles are released from the cells via a budding process to produce infectious progeny viruses. Herein, the F protein of Newcastle virus is involved in the fusion process between the viral envelope and the cytoplasm membrane to promote virus infectivity in the cell. Specifically, the F protein is present in the form of an inactive precursor (F0) in the virion. When the virion attaches to the host cells using viral HN protein, the inactive precursor F0 is cleaved into active subunits F1 and F2 by the protease of the host cells. The subunits F1 and F2 thus lead to membrane fusion between virion and cell.

It is known that the virulence of Newcastle disease virus depends on how easily the inactive precursor F0 is cleaved into the active subunits F1 and F2 in susceptible host cells. Pathogenic Newcastle disease virus having a polybasic amino acid sequence (-Arg/Lys-Arg-Gln-Lys/Arg-Arg-Phe-) (SEQ ID NO: 12) at the F1/F2 cleavage site can be easily cleaved by ubiquitous proteases in a wide range of host cell types, whereas non-pathogenic Newcastle disease virus has no polybasic amino acid sequence, and for this reason, the cleavage sites can be cleaved only by trypsin-like enzymes, which are found in limited areas such as respiratory mucosal tissue.

Tentative diagnosis of Newcastle disease can be determined based on the clinical signs of affected birds and epidemiological history. Definite diagnosis should be achieved by laboratory tests. Laboratory tests for diagnosis of Newcastle disease generally include methods for detection of Newcastle disease virus antigen and/or antibody that are specific for Newcastle disease virus.

The antigen detection methods using a few tissue samples containing high titered viral load from diseased chickens or dead chickens are effective in diagnosing Newcastle disease. Currently available antigen detection methods include virus isolation, reverse transcriptase-polymerase chain reaction (RT-PCR), and enzyme-linked immunosorbent assay (ELISA).

The antibody detection methods can be used to detect Newcastle disease virus specific antibodies in unvaccinated poultry or to measure significantly increased antibody titer in vaccinated poultry after onset of outbreak. Currently available antibody detection methods include hemagglutination inhibition (HI) test, virus neutralization (VN) test, and enzyme-linked immunosorbent assay (ELISA). The antibody detection methods are very effective in testing large-scale samples, because they can be performed in living chickens and can test a large amount of samples within a short time compared to the antigen detection methods. However, currently available antibody detection methods have a disadvantage in that they cannot differentiate infected individuals from vaccinated individuals.

In most of the areas or countries with disease outbreaks or at risk, vaccination is performed in order to protect susceptible chickens from Newcastle disease. In these areas, some vaccinated but unsolid immunized chickens can be infected with pathogenic Newcastle virus. Most of such chickens show subclinical symptoms without any death, but can shed a small amount of pathogenic Newcastle virus through feces or respiratory organs. Chickens carrying Newcastle disease virus thus can be considered as a reservoir that may play an important role in spreading disease. This is because, on farms in which several tens of thousands of chickens are raised, it is difficult to detect some virus-harbouring chickens in a chicken flock by clinical inspection alone. Currently the most reliable method is to use specific pathogen-free (SPF) chickens as sentinel birds in order to detect pathogenic Newcastle disease virus circulating in the chicken flock. However, this method is not very suitable, because the purchase and management of the sentinel chickens are very troublesome and, in addition, the sentinel chickens can act as a source of spreading contagious diseases. The antigen detection methods can be a method to detect infected chickens among uninfected chickens, but it is also not suitable, because the titer of virus shed from vaccinated and infected chickens is low and these methods are not practical to test a large number of chickens at the same time.

The most effective method of detecting infected chickens among a large-scale chicken flock at the same time is to use a serological test method that can differentiate infected from vaccinated animals (DIVA). Currently available serological test methods include a hemagglutination inhibition (HI) test method and an enzyme-linked immunosorbent assay. However, these methods cannot differentiate infected animals from vaccinated animals. Therefore, plausible strategies for realizing the differentiation between infected and vaccinated animals (DIVA) are generally classified into two categories. The first method is a method comprising vaccination in chicken with a marker vaccine with lack of non-protective Newcastle disease viral protein, and examining the presence of antibodies to the deleted protein in birds. This strategy requires obligatory use of the marker vaccine instead of the current whole virus. The second method employs a diagnostic method for detecting an antibody to an antigenic site (epitope) that is present only in pathogenic Newcastle disease virus. However, this diagnostic method is not yet developed.

SUMMARY OF THE INVENTION

The present invention relates to synthetic peptide fragments comprising amino acid sequences of specific antigen sites of pathogenic Newcastle disease virus in birds, and more particularly to novel synthetic peptide fragments that comprise polybasic amino acid sequences at the cleavage site of the F protein of pathogenic Newcastle disease virus and that induce humoral immune responses in hosts while reacting only with antibodies to pathogenic Newcastle disease virus and are useful to differentiate infected individuals from vaccinated individuals.

The present inventors have conducted extensive studies to identify antigenic sites (epitopes) specifically present only in pathogenic Newcastle disease virus in order to develop a serological test method that can differentiate infected individuals from vaccinated individuals. As a result, the present inventors have established that, unlike nonpathogenic Newcastle disease virus, pathogenic Newcastle disease virus has a pathogenic virus-specific motif containing polybasic amino acid sequences and phenylalanine in the F1/F2 cleavage site of the F protein and the motif induces immunogenic and antigenic, and that synthetic peptide fragments mimicking the motif react specifically with antibodies to pathogenic Newcastle disease virus but not with antibodies to nonpathogenic Newcastle disease virus (vaccine antibodies), thereby completing the present invention.

Therefore, the objective of the present invention is to provide synthetic peptide fragments mimicking pathogenic virus-specific motif that can differentiate infected individuals from vaccinated individuals and evaluate the immunity level of Newcastle disease-infected animals in vivo.

Another objective of the present invention is to provide various Newcastle disease diagnostic compositions, diagnostic kits and diagnostic strips that comprise said synthetic peptide fragments.

Another objective of the present invention is to provide a diagnostic method that uses said Newcastle disease diagnostic compositions, diagnostic kits and diagnostic strips.

To achieve the above objectives, in one aspect, the present invention provides synthetic peptide fragments of SEQ ID NOS 1 to 5 containing amino acid sequences of pathogenic virus-specific motif of the F protein of pathogenic Newcastle disease virus, in which the antigenic sites of the motif possess immunogenic and antigenic properties and are specific for pathogenic Newcastle disease virus, as well as their modified peptides.

In another aspect, the present invention provides various Newcastle disease diagnostic compositions, diagnostic kits and diagnostic strips that comprise said synthetic peptide fragments or their modified peptides.

In another aspect, the present invention provides diagnostic methods that use said Newcastle disease diagnostic compositions, diagnostic kits or diagnostic strips.

BRIEF DESCRIPTION OF THE DRAWINGS

The above and other objectives, features and advantages of the present invention will be apparent from the following detailed description of the preferred embodiments of the invention in conjunction with the accompanying drawings, in which:

FIG. 4 is a schematic diagram showing an immunochromatographic method for detection of pathogenic Newcastle disease virus antibodies using peptide fragments according to the present invention; and FIG. 5 shows the results of an immunochromatographic test, which indicate that peptides according to the present invention react specifically with antibodies to Newcastle disease virus.

DETAILED EXPLANATION OF THE INVENTION

Figure 1:
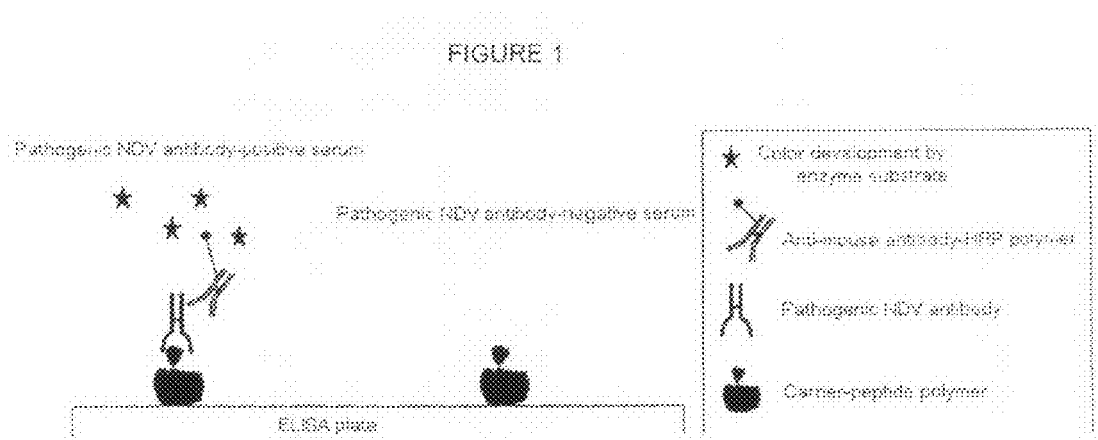
FIG. 1 is a schematic diagram showing an enzyme-linked immunosorbent assay (ELISA) for detection of antibodies to pathogenic Newcastle disease virus using peptide fragments according to the present invention.
Figure 2:
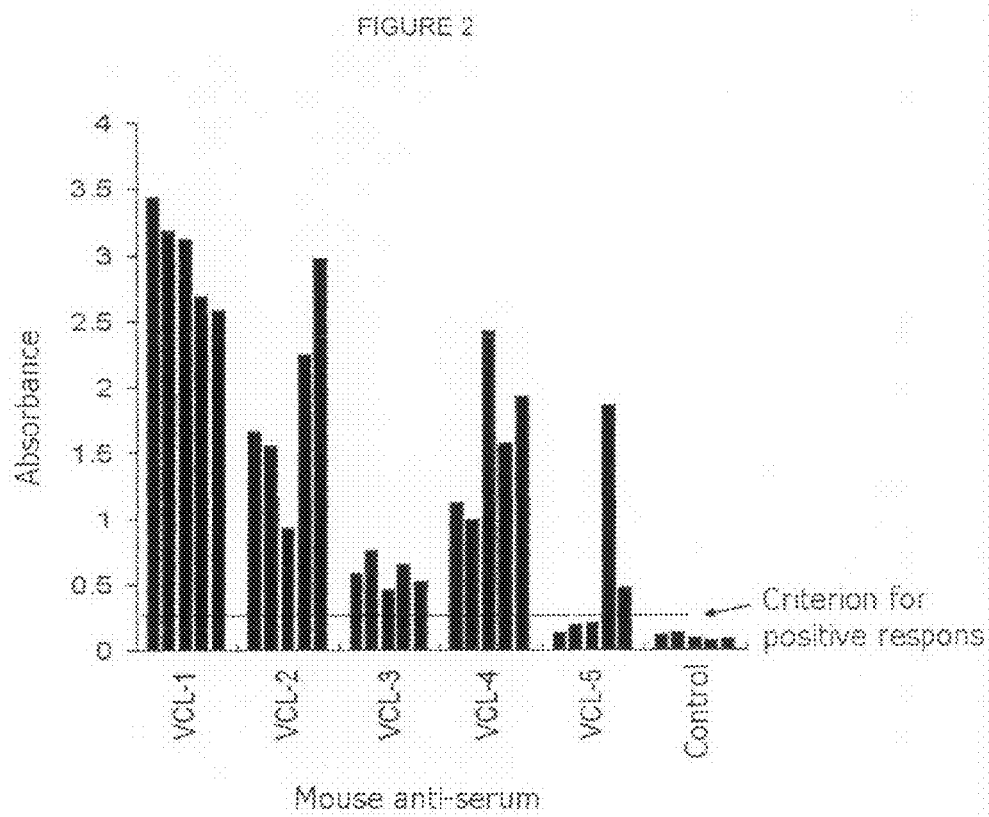
FIG. 2 shows the results of enzyme-linked immunosorbent assay (ELISA) for humoral immune responses in mice immunized with peptide fragments according to the present invention.

Hereinafter, the present invention will be described in further detail.

The present invention relates to an antigenic site that possesses immunogenic and antigenic properties and, at the same time, is present specifically in pathogenic Newcastle disease virus, as well as synthetic peptide fragments containing the antigenic site.

As used herein, the term "antigenic sites of polybasic amino acid sequences of pathogenic Newcastle disease virus F protein" refers to antigenic motifs containing polybasic amino acid sequences, which are commonly present in the F protein of Newcastle disease virus with an intracerebral pathogenicity index (ICPI) of more than 0.7, in which the sites react with antibodies induced by host immune responses. For example, pathogenic Newcastle disease viruses, which are recently prevalent in Korea, all have a polybasic amino acid motif, -Arg-Arg-Gln-Lys-Arg-Phe- (SEQ ID NO: 1), whereas the nonpathogenic Newcastle disease virus strains such as LaSota strain or B1 strain, which are widely used as Newcastle disease vaccines in Korea, have an amino acid motif of -Gly-Arg-Gln-Gly-Arg-Leu- (SEQ ID NO: 6).

The inventive synthetic polypeptide fragments, which are polybasic amino acid sequences present in pathogenic Newcastle disease virus, contain amino acid sequences set forth in Table 1 below.

TABLE 1

| SEQ ID NOS: | Amino acid sequences |
|---|---|
| 1 | Arg-Arg-Gln-Lys-Arg-Phe |
| 2 | Lys-Arg-Gln-Lys-Arg-Phe |
| 3 | Arg-Arg-Gln-Arg-Arg-Phe |
| 4 | Gln-Arg-Gln-Arg-Arg-Phe |
| 5 | Arg-Arg-Arg-Lys-Arg-Phe |

The inventive peptide fragments of SEQ ID NOS: 1 to 5 may be conjugated with a carrier such as ovalbumin or bovine serum albumin in order to increase the reactivity to the pathogenic Newcastle disease virus antibodies. In addition, the inventive peptide fragments can be conjugated with a carrier such as keyhole limpet hemocyanin (KLH) in order to increase the immunogenicity.

Furthermore, the peptide fragments of SEQ ID NOS: 1 to 5 according to the present invention may also be used in the modified form of peptides, obtained by adding Cys-Ala-Ala to the N terminus of the peptides in order to conjugate the peptides with a carrier such as ovalbumin or bovine serum albumin, adding Ile to the C terminus and then attaching an amino group ($NH_2$) to the C terminus in order to stabilize the morphologic features of the peptides.

Although synthetic technology for preparing the peptides according to the present invention is not specifically limited, synthesis of peptides using the Fmoc solid phase synthesis procedure, and then purifying the peptides by a HPLC method using a Waters C18 column, is preferably used. This preparation technology is well known in the field.

The synthetic peptide fragments of SEQ ID NOS: 1 to 5 according to the present invention can be used to prepare various compositions or kits for diagnosing Newcastle disease, which are useful to differentiate infected individuals from vaccinated individuals. For the preparation of compositions or kits for diagnosing Newcastle disease, the peptide fragments of the present invention are preferably conjugated with a carrier such as ovalbumin or bovine serum albumin. In addition, enzyme-linked immunosorbent assay (ELISA) diagnostic kits comprising the peptide fragments can be used to test massive samples, and rapid immunochromatographic diagnostic kits can also be prepared for simple and easy pen-side tests. However, because the amino acid sequences of the peptides according to the present invention were identified, those skilled in the field can easily prepare diagnostic compositions or diagnostic kits for Newcastle disease, using conventional techniques known in the field, and such diagnostic compositions or diagnostic kits are included in the scope of the present invention.

The peptide fragments of SEQ ID NOS: 1 to 5 according to the present invention contain the polybasic amino acid sequences present specifically on the F protein of pathogenic Newcastle disease virus. These polybasic amino acid sequences are not present in nonpathogenic Newcastle disease virus, and the regions comprising the motifs of the polybasic amino acid sequences possess antigenic property, and thus facilitate differentiating chickens infected with pathogenic Newcastle disease virus from chickens vaccinated with a Newcastle disease vaccine. Therefore, the present invention allows a differentiating infected from vaccinated animals (DIVA) strategy even under current vaccination strategies, and thus makes it easy to control and eradicate Newcastle disease, through current Newcastle vaccination policy.

It was proved that, when the peptide fragments of the present invention are applied to enzyme-linked immunosorbent assays (ELISA) or immunochromatography assays, which are generally used for massive testing or rapid tests, they can differentiate infected animals from vaccinated animals, indicating that diagnostic kits can be prepared even when other diagnostic methods are applied. Particularly, enzyme-linked immunosorbent assay (ELISA) kits have advantages in that they can test massive samples within short turnaround for detection of the infected birds among the vaccinated chicken flock. Accordingly, these kits can either eliminate the source of spreading Newcastle disease rapidly by detecting and removing infected chickens through serological monitoring or improve the immune status of chicken flocks by modifying Newcastle disease vaccination programs. Therefore, these kits can be very effectively applied in Newcastle disease eradication programs.

Moreover, because the peptide fragments of the present invention can be produced using protein synthesizers only through amino acid sequence information without handling any pathogen or pathogen-derived gene, the purities of antigens in the peptide fragments are high. In addition, according to the present invention, it is possible to prepare standardized diagnostic reagents, because it is easy to quantify antigens. Furthermore, the present invention ensures the safety of diagnostic kits, because there is no need to handle infectious pathogens in preparing the diagnostic kits.

In another aspect, the present invention provides kits for diagnosing Newcastle disease, comprising peptide fragments of SEQ ID NOS: 1 to 5 or their modified peptides, and methods of diagnosing Newcastle disease using the same.

In another aspect, the present invention provides immunochromatographic strips for diagnosing Newcastle disease, comprising peptide fragments of SEQ ID NOS: 1 to 5 or their modified fragments.

The strips for diagnosing Newcastle disease can be prepared by stacking a sample pad, a membrane having peptide fragments of SEQ ID NOS: 1 to 5 or their modified peptides absorbed thereon, a pad containing gold particles, and an absorbent pad on each other. Herein, the membrane is made of nitrocellulose, and the sample pad and the absorbent pad are made of cellulose.

In another aspect, the present invention provides a method of diagnosing Newcastle disease through immunochromatography using a housing that comprises said strip for diagnosing Newcastle disease, a sample application hole and a result display window and is manufactured such that the strip can be inserted therein to observe test results.

PREFERRED EMBODIMENTS OF THE INVENTION

Example 1

Synthesis of Peptides of SEQ ID NOS: 1 to 5

The synthesis of peptides of SEQ ID NOS: 1 to 5 was performed using the known 9-fluorenylmethyloxycarbonyl (Fmoc) solid phase synthesis procedure, and the amino acid sequences for the synthesis of the peptides were the same as SEQ ID NOS: 1 to 5.

The synthesis of amino acid sequences was performed in the reverse order of the amino acid sequence of the desired synthetic fragment, that is, the adhesion of resin started from the C-terminal amino acid.

(1) Wang resin was added to 2 ml of N,N-dimethylformamide (DMF) at final concentration of 25 μmol and swelled for 20 minutes.

(2) The resin was washed twice with 2 ml of N-methyl-2-pyrrolidinone (NMP).
(3) The resin was treated twice with 1.5 ml of an Fmoc deprotection solution 20% piperidine in DMF) for 10 minutes each time.
(4) The resin was washed twice with 2 ml of N-methyl-2-pyrrolidone (NMP).
(5) 8 equivalents of Fmoc leucine was stirred in 8 equivalents (0.6 ml) of dicyclohexylcarbodiimide (DCC) and 8 equivalents (0.6 ml) of N-hydroxy-benzotriazole (HoBt) for 2 hours to polymerize the resin with amino acid.
(6) The resin was washed twice with 2 ml of methanol (MeOH) for 30 sec each time.
(7) The resin was washed twice with 2 ml of NMP.
(8) The steps (3)-(7) were repeated until the synthesis of the amino acid sequence of SEQ ID NO: 1 was completed.
(9) After NMP was completely removed from the resin, the resin was treated with a cleavage reagent (950 µl of trifluoroacetic acid, 25 µl of tri-isopropyl silane and 25 µl of water) for 2 hours to cleave the synthetic polypeptide from the resin.
(10) A precipitating solution (ether: hexanes=2:1) was added to the synthetic polypeptide product and centrifuged for 5 minutes, and the supernatant was removed.
(11) The precipitated synthetic polypeptide was purified by high-performance liquid chromatography (HPLC) using a 0.01% TFA-containing acetonitrile/water concentration gradient solvent system over 50 minutes, wherein the concentration gradient ranged from 5% to 100%. The purified fraction was freeze-dried to obtain a white powdery compound. The used HPLC system was a Waters 2690 system, the used column was Waters C18 (5 micron), and the detection was performed at a wavelength of 220-270 nm. Mass analysis was performed using an HP 1100 series LC/MSD model.

Example 2

Synthesis of Modified Peptides

In order to conjugate the peptide fragments with a carrier before use, Cys-Ala-Ala was added to the N-terminus of the amino acid sequences of the peptides of SEQ ID NOS: 1 to 5. Then, for the morphological stabilization of the peptides, Ile was added to the C-terminus, and then an amino group (NH$_2$) was additionally added thereto. For the C-terminal amidation of the peptide fragments, amide resin was used instead of the Wang resin used in Example 1, at the same concentration. The synthesis process was performed in the same manner as in Example 1, except that, in order to attach cysteine to the N-terminus, the final synthetic amino acid glycine (Gly) was attached to the resin, and then cysteine was additionally attached thereto.

Example 3

Synthesis of Ovalbumin-Conjugated Peptides

Ovalbumin was conjugated to the synthetic peptides prepared in Example 2. 2 mg of each of the synthetic polypeptide products was dissolved in 100 µl of distilled water. Then, 2 mg of a carrier protein was dissolved in PBS/5 mM EDTA buffer and mixed with each of the peptides, and the mixture was allowed to react at room temperature for 2 hours.

Example 4

Synthesis of Bovine Serum Albumin-Conjugated Peptides

Bovine serum albumin was conjugated to the synthetic peptides prepared in Example 2. The synthesis process was performed in the same manner as in Example 3, and 2 mg of each of the synthetic polypeptide products was dissolved in 100 µl of distilled water. Then, 2 mg of a carrier protein was dissolved in PBS/5 mM EDTA buffer and mixed with each of the peptides, and the mixture was allowed to react at room temperature for 2 hours.

Example 5

Synthesis of Keyhole Limpet Hemocyanin-Conjugated Peptides

Keyhole limpet hemocyanin was conjugated to the synthetic peptides prepared in Example 2. The synthesis process was performed in the same manner as in Example 3, and 2 mg of each of the synthetic polypeptide products was dissolved in 100 µl of distilled water. Then, 2 mg of a carrier protein was dissolved in PBS/5 mM EDTA buffer and mixed with each of the peptides, and the mixture was allowed to react at room temperature for 2 hours.

Example 6

Preparation of Mouse Anti-Peptide Immune Sera

The synthetic peptide—Keyhole limpet hemocyanin conjugates prepared in Example 5 were mixed with the same amount of complete Freund's adjuvant, and then each of the peptides was inoculated subcutaneously into five mice in an amount of 30 µg/mouse. The immunized mice were boosted 2 weeks after first immunization with the same peptide in incomplete Freund's adjuvant according to the same immunization method as described above. Blood was collected one week after final immunization from the mice in order to prepare immune sera. The prepared immune sera were named as shown in Table 2 below and stored at −20° C. before use in experiments.

TABLE 2

| Modified peptides (SEQ ID NOS: 7 to 11) conjugaged to KLH | | |
|---|---|---|
| Immune sera | Conjugate of KLH-Immune peptide fragments | SEQ ID NO |
| VCL-1 | KLH-Cys-Ala-Ala-Arg-Arg-Gln-Lys-Arg-Phe-Ile-NH$_2$ | 7 |
| VCL-2 | KLH-Cys-Ala-Ala-Lys-Arg-Gln-Lys-Arg-Phe-Ile-NH$_2$ | 8 |

TABLE 2-continued

Modified peptides (SEQ ID NOS: 7 to 11) conjugaged to KLH

| Immune sera | Conjugate of KLH-Immune peptide fragments | SEQ ID NO |
|---|---|---|
| VCL-3 | KLH-Cys-Ala-Ala-Arg-Arg-Gln-Arg-Arg-Phe-Ile-NH$_2$ | 9 |
| VCL-4 | KLH-Cys-Ala-Ala-Gln-Arg-Gln-Arg-Arg-Phe-Ile-NH$_2$ | 10 |
| VCL-5 | KLH-Cys-Ala-Ala-Arg-Arg-Arg-Lys-Arg-Phe-IIe-NH$_2$ | 11 |

Example 7

Preparation of Enzyme-Linked Immunosorbent Assay (ELISA) Plate

Each of the bovine serum albumin-peptide conjugates (Example 3) and the ovalbumin-peptide conjugates (Example 4) was diluted in 0.01 M phosphate buffered saline (pH 7.2) to a concentration of 0.5 µg/ml, and each of the dilutions was added to an ELISA plate at a rate of 50 µl/well and adsorbed to the wells at 37° C. for 2 hours (hereinafter referred to as "test wells"). For a control test, bovine serum albumin or ovalbumin alone was diluted in phosphate buffered saline at a concentration of 0.5 µg/ml, and then adsorbed to the well of the ELISA plate in the same conditions as described above (hereinafter referred to as "control well"). Three wells of the ELISA plate were used per test serum sample, and among them, two wells were test wells, and the remaining one well was a control well. The coated ELISA plate was washed three times with washing buffer (0.002 M phosphate buffered saline, pH 7.2, 0.01% Tween 20). Thereafter the ELISA plate was completely dried, sealed with a sealing tape, and then stored at 4° C. before use in experiments.

Example 8

Preparation of Immunochromatography Strips

Two mg/ml of each of the bovine serum albumin-peptide conjugates prepared in Example 4 was used as an antigen coated at test line of a nitrocellulose membrane. Namely, each of the peptide fragments was coated on the test line position (line for detecting antibodies to pathogenic Newcastle disease virus), and the same concentration of goat anti-mouse antibody was coated at the control line position.

Figure 3:
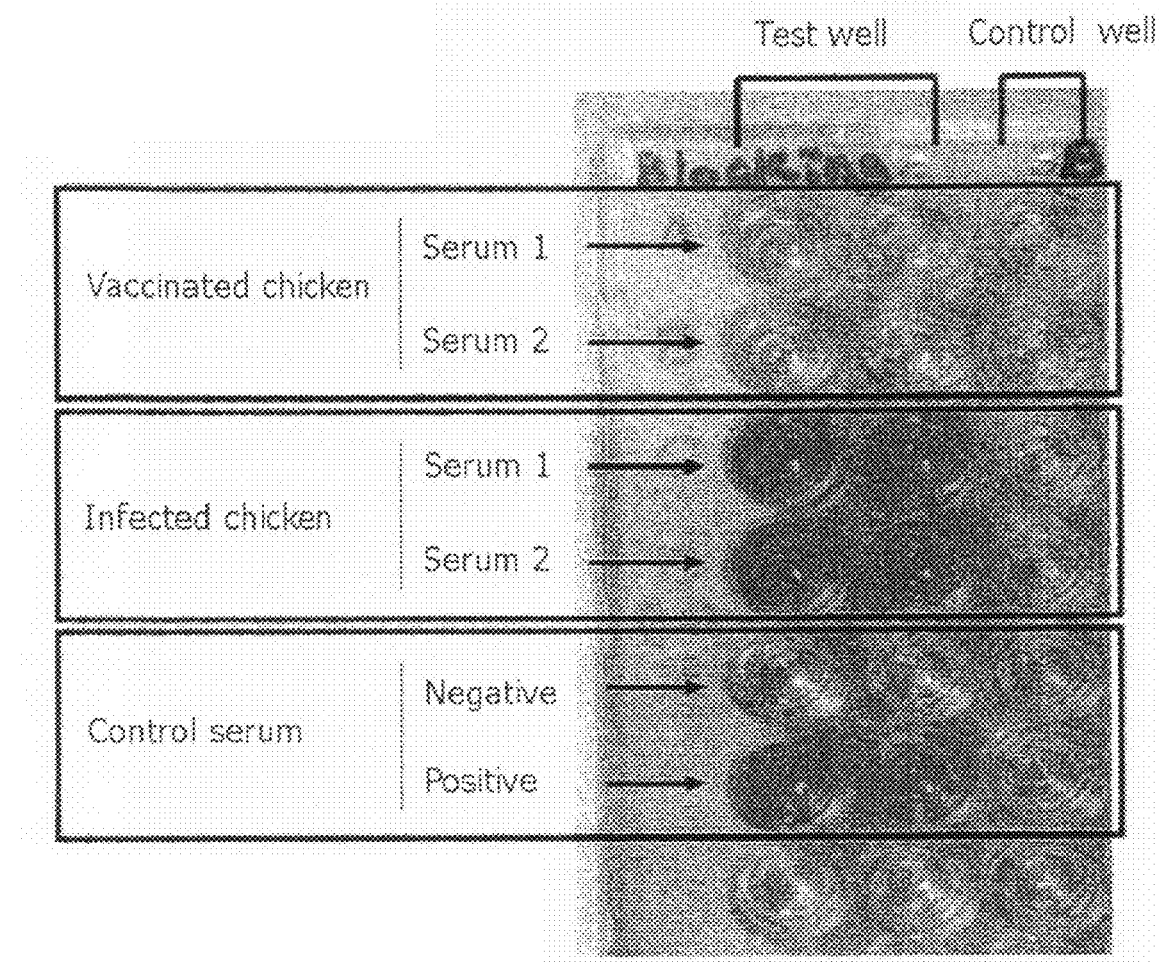
FIG. 3 is a graphic diagram showing the results of enzyme-linked immunosorbent assay (ELISA), which indicate that peptide fragments according to the present invention specifically detect antibodies to pathogenic Newcastle disease virus.

Anti-chicken IgY mouse monoclonal antibody was conjugated to gold colloids at a concentration of 20 µg per g of gold colloids. Specifically, gold chloride was reduced with a sodium citrate solution to prepare plain gold, to which the antibody was then added, thus preparing antibody-conjugated gold particles having a size of 40 nm and showing an absorbance of 10±1 at 532 nm. To stabilize the conjugated antibody, the gold particles were treated with a PEG solution. The gold-conjugated antibody was added in an amount of 8.3 μl/strip, and polyester or glass was wetted with the conjugated antibody and dried, thus preparing a gold pad. An absorbent pad and a sample pad were prepared through a drying process such that a reaction solution could be easily absorbed into the pads. The sample pad and the absorbent pad were made of cellulose.

The above-prepared membrane and pads were stacked in the order of the sample pad, the gold pad, the nitrocellulose membrane and the absorbent pad starting from the right side, and the immunochromatography strip, cut to a size of 4.45 mm/strip, was placed on the lower plate of a device and covered with an upper plate, thus preparing a diagnostic kit.

Experimental Example 1

Evaluation of Immunogenicity of Novel Peptide Fragments

In order to examine whether the peptide fragments of the present invention induce immune responses in animals, an enzyme-linked immunosorbent assay (ELISA) was performed using the mouse anti-peptide immune sera shown in Table 2 (FIG. 1). Specifically, to the two test wells and one control well of the ELISA plate of Example 7 having each of the ovalbumin-peptide conjugates adsorbed thereto, serum diluted stepwise in reaction buffer (0.01 M phosphate buffered saline, pH 7.2, 2% BSA, 0.05% Tween 20) was added at a rate of 100 μl/well, and then allowed to react at 37° C. for 1 hour. Then, the ELISA plate was washed three times with washing buffer. Peroxidase conjugated anti-mouse IgG, diluted in reaction buffer at a concentration of 0.5 μg/ml, was added at a rate of 100 μl/well and allowed to react at 37° C. for 40 minutes, and then the ELISA plate was washed three times with washing buffer. To the wells of the ELISA plate, a substrate solution (0.04% O-phenylenediamine dihydrochloride, 0.01% hydrogen peroxide in citrate-phosphate buffer) was added at a rate of 100 μl/well and allowed to react for 10 minutes, then stop solution (0.1N hydrochloric acid) was added at a rate of 50 μl/well to all wells. Then, the degree of color development in each of the wells was measured at an absorbance of 450 nm. In the results of enzymatic reactions, in the case of the samples containing antibodies infected with Newcastle disease virus, the final reaction solutions in the tested wells developed a yellow color. The result of test of each serum was analyzed using net absorbance, obtained by subtracting the absorbance of the control well from the absorbance of the test well.

The test results are shown in FIG. 2. As shown in FIG. 2, the mouse immune sera (VCL-1, VCL-2 and VCL-4) immunized with the inventive synthetic peptide fragments comprising each of the amino acid sequences of SEQ ID NOS: 1, 2 and 4 all induced strong immune responses to the bovine serum albumin-peptide conjugate comprising the same sequences. In addition, in the case of the mouse sera (immune sera VCL-3 and VCL-5) immunized with each of the inventive peptide fragments of SEQ ID NOS: 3 and 5, either an immune response occurred only in some individuals or a weak immune response was shown.

Experimental Example 2

Test of Differentiating Infected Individuals from Vaccinated Individuals Using Prepared ELISA Plate In order to examine whether the application of the inventive peptide fragments (comprising each of the amino acid sequences of SEQ ID NOS: 1 to 5) to an enzyme-linked immunosorbent assay (ELISA) allows differentiating infected animals from vaccinated chickens, the ELISA plate of Example 7, having each of the bovine serum albumin-peptide conjugates adsorbed thereto, was used. The following chickens were used in this Experimental Example: 5 chicken sera collected at 3 weeks after inoculation with a Newcastle La Sota vaccine; 5 chicken sera showing a negative response to Newcastle disease; and 4 chickens that survived after experimental infection with pathogenic Newcastle disease virus (7 days after infection). Each of the sera was diluted in reaction buffer (0.01 M phosphate buffered saline, pH 7.2, 2% BSA, 0.05% Tween 20) at 1:500, and each of the dilutions was added to two test wells and one control well at a rate of 100 μl/well, and then allowed to react at 37° C. for 1 hour. Then, the ELISA plate was washed three times with washing buffer. Peroxidase conjugated anti-chicken IgG, diluted in reaction buffer at a concentration of 0.5 μg/ml, was added to the ELISA plate at a rate of 100 μl/well and allowed to react 37° C. for 40 minutes, and then the ELISA plate was washed three times with washing buffer. To the wells of the ELISA plate, a substrate solution (0.04% O-phenylenediamine dihydrochloride, 0.01% hydrogen peroxide in citrate-phosphate buffer) was added at a rate of 100 μl/well and allowed to react for 10 minutes, then stop solution (0.1N hydrochloric acid) was added at a rate of 50 μl/well to all wells. Then, the degree of color development in each of the wells was measured at an absorbance of 450 nm. In the results of enzymatic reactions, in the case of the samples containing antibodies infected with Newcastle disease virus, the final reaction solutions in the tested wells developed a yellow color (FIG. 3). The result of test of each serum was analyzed using net absorbance, obtained by subtracting the absorbance of the control well from the absorbance of the test well, and the test results are shown in Table 3 below.

In evaluating the test results, a new absorbance higher than the average net absorbance of negative control serum×2.5 was considered to be a positive response.

inhibition (HI) test method showed a positive response to Newcastle disease antibodies (HI titer of 4 or more) in both the vaccinated sera and the infected sera, suggesting that the HI test method could not differentiate the infected animals from the vaccinated animals. Accordingly, the results of this Experimental Example indicate that the peptide fragments of the present invention can differentiate infected individuals from vaccinated individuals.

Experimental Example 3

Figure 4:
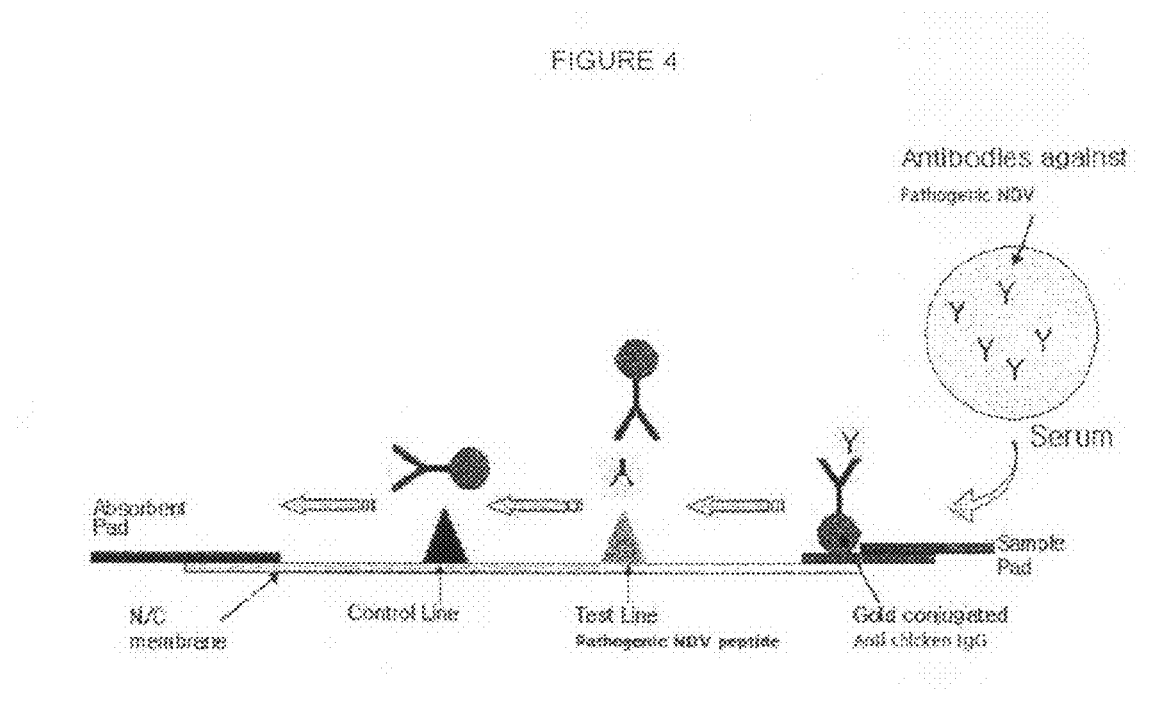

Test of Differentiating Infected Individuals from Vaccinated Individuals Using Immunochromatography Assay In order to examine whether immunochromatography assay using the inventive peptide fragments of SEQ ID NOS: 1-5 can differentiate infected chickens from vaccinated chickens, the immunochromatography assay kit prepared in Example 8 was used. The antigen coated on the assay kit was the peptide-bovine serum albumin conjugate comprising the amino acid sequence of SEQ ID NO: 1. Sera used in this Experimental Example were collected from vaccinated chicken, NDV antibody-negative chicken, pathogenic NDV-infected chicken, and NDV-negative chicken. A 50 μl volume of each of the test sera was applied to the diagnostic kit and then after 10 minutes the test results were read. The principle of detecting pathogenic Newcastle disease virus antibodies by immunochromatography assay is shown in FIG. 4. As shown in FIG. 4, when the pathogenic Newcastle disease virus antibodies are present in sera, these antibodies primarily bound to anti-IgY monoclonal antibody conjugated with gold particles on the gold pad and then the gold-monoclonal antibody-serum antibody complex move along the membrane according to the principle of immunochromatography and bound to the peptide on the test line and to anti-mouse immunoglobulins on the control line. This results in formation of two purple bands together with the control band on the mem-

TABLE 3

Results of enzyme-linked immunosorbent assay (ELISA) using inventive peptide fragments

| | | ELISA of present invention | | | | | |
|---|---|---|---|---|---|---|---|
| | Number of animals | SEQ ID NO: 1* | SEQ ID NO: 2 | SEQ ID NO: 3 | SEQ ID NO: 4 | SEQ ID NO: 5 | HI test |
| Vaccinated chickens | 5 | 0/5(0.11)** | 0/5(0.27) | 0/5(0.70) | 0/5(0.07) | 0/5(0.60) | 5/5(8.0)*** |
| Infected chickens | 4 | 4/4(2.21) | 4/4(2.33) | 4/4(2.45) | 4/4(1.39) | 4/4(1.91) | 4/4(6.0) |
| Negative chickens | 5 | 0/5(0.14) | 0/5(0.32) | 1/5(0.81) | 0/5(0.09) | 0/5(0.81) | 0/5(<2.0) |
| Criteria for positive response | | 0.15**** | 0.73 | 0.95 | 0.13 | 1.60 | |

*peptide-bovine serum albumin conjugate comprising the respective amino acid sequences;
**number of positive chickens/number of tested chickens (average ELISA absorbance value of test sera);
***number of positive chickens/number of tested chickens (average HI log2 titer of tested sera); and
****Absorbance as criteria for positive response (absorbance of negative control serum × 2.5).

As shown in Table 3, the ELISA results of the present invention were compared with the results of the hemagglutination inhibition (HI) test method, which is the most widely-used antibody test method. As shown in Table 3 above, the peptide fragments of the present invention all showed a positive response in the sera of the chickens infected with pathogenic Newcastle disease virus. However, the peptide fragments of the present invention all showed a negative response in the vaccinated chickens. Meanwhile, the hemagglutination brane. Meanwhile, if there is no pathogenic Newcastle disease virus antibody in the sample, anti-IgY monoclonal antibody conjugated with gold particles on the gold pad move along the membrane, and then bind to anti-mouse immunoglobulins on the control line. This results in formation of one purple band on the control line (because the monoclonal antibody conjugated to gold particles is antibody of mouse origin, it binds directly to anti-mouse antibody at the control line).

The results of the immunochromatography assay are shown in FIG. 5. As shown in FIG. 5, the chicken serum infected with pathogenic Newcastle disease virus showed a positive response, but the vaccinated chicken serum and the negative chicken serum showed a negative response. From such results, it can be seen that the immunochromatography assay using the peptide fragments of the present invention can also sufficiently differentiate infected chickens from vaccinated chickens.

As described above, the present invention can provide specific antigenic sites of Newcastle disease virus, which can be used to differentiate infected individuals from vaccinated individuals and to evaluate the immunity level of Newcastle disease-infected animals in vivo. Using such antigenic sites, the present invention can provide novel peptide fragments useful to differentiate infected individuals from vaccinated individuals and can provide useful information for the preparation of various Newcastle disease diagnostic compositions, diagnostic kits and diagnostic strips that comprise the peptide fragments.

Furthermore, unlike prior antibody-detecting diagnostic reagents, the peptide fragments of the present invention allow the preparation of various diagnostic reagents for testing serum that can differentiate infected individuals from vaccinated individuals by specifically detecting pathogenic Newcastle disease virus antibodies. Particularly, diagnostic methods employing the peptide fragments of the present invention can differentiate infected chickens from vaccinated chickens in the area in which Newcastle disease vaccination is performed, and thus the methods are very effective in establishing Newcastle disease eradication programs such as large-scale surveillance of Newcastle disease.

Although the preferred embodiment of the present invention has been described for illustrative purposes, those skilled in the field will appreciate that various modifications, additions and substitutions are possible, without departing from the scope and spirit of the invention as disclosed in the accompanying claims.

What is claimed is:

1. A kit for diagnosing Newcastle disease, comprising the peptide of SEQ ID NO: 7.

2. The kit of claim 1, wherein the peptide of SEQ ID NO: 7 further comprises bovine serum albumin attached to the N-terminus of the peptide.

3. The kit of claim 1, wherein of SEQ ID NO: 7 is a peptide reacting specifically with antibodies to pathogenic Newcastle disease virus.

4. The kit of claim 1, wherein the kit is used to differentiate individuals infected with pathogenic Newcastle disease virus from vaccinated individuals.

5. A method of diagnosing Newcastle disease by an enzyme-linked immunoabsorbent assay (ELISA) using the kit of claim 1.

6. A method of diagnosing Newcastle disease by an enzyme-linked immunoabsorbent assay (ELISA) using the kit of claim 2.

7. A method of diagnosing Newcastle disease by an enzyme-linked immunoabsorbent assay (ELISA) using the kit of claim 3.

8. An immunoassay strip for screening for antibodies to a pathogenic Newcastle disease virus in chickens, comprising:
A) a sample pad;
B) a pad comprising gold-conjugated anti-chicken IgY mouse monoclonal antibodies;
C) a nitrocellulose membrane comprising the peptide of SEQ ID NO: 7 coupled thereto;
D) and an absorbant pad;
said immunoassay strip being prepared by stacking in the order: A), B), C), and D).

9. The immunoassay strip of claim 8, wherein the peptide of SEQ ID NO: 7 further comprises bovine serum albumin attached to the N-terminus of the peptide.

10. The immunoassay strip of claim 8, wherein the peptide of SEQ ID NO: 7 is a peptide reacting specifically with antibodies to pathogenic Newcastle disease virus.

11. The immunoassay strip of claim 8, wherein the strip is used to differentiate individuals infected with pathogenic Newcastle disease virus from vaccinated individuals.

12. A method of diagnosing Newcastle disease by an enzyme-linked immunoabsorbant assay (ELISA) using the immunoassay strip of claim 8.

13. A method of diagnosing Newcastle disease by an enzyme-linked immunoabsorbent assay (ELISA) using the immunoassay strip of claim 9.

14. A method of diagnosing Newcastle disease through an enzyme-linked immunoabsorbent assay (ELISA) using the immunuoassay strip of claim 10.

* * * * *

```
                          SEQUENCE LISTING

<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Synthetic construct

<400> SEQUENCE: 1

Arg Arg Gln Lys Arg Phe
 1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic construct

<400> SEQUENCE: 2

Lys Arg Gln Lys Arg Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic construct

<400> SEQUENCE: 3

Arg Arg Gln Arg Arg Phe
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic construct

<400> SEQUENCE: 4

Gln Arg Gln Arg Arg Phe
 1               5
```

```
<210> SEQ ID NO 5
<211> LENGTH: 6
<212> TYPE: PRT
<213> ORGANISM: Artificial Sequence
<220> FEATURE:
<223> OTHER INFORMATION: Synthetic construct

<400> SEQUENCE: 5

Arg Arg Arg Lys Arg Phe
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic construct

<400> SEQUENCE: 6

Gly Arg Gln Gly Arg Leu
 1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 10

<400> SEQUENCE: 7

Cys Ala Ala Arg Arg Gln Lys Arg Phe Ile
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 10

<400> SEQUENCE: 8

Cys Ala Ala Lys Arg Gln Lys Arg Phe Ile
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 10

<400> SEQUENCE: 9

Cys Ala Ala Arg Arg Gln Arg Arg Phe Ile
 1               5                  10

<210> SEQ ID NO 10
<211> LENGTH: 10
<212> TYPE: PRT
<213> ORGANISM: Artificial Sequence
```

```
-continued

<220> FEATURE:
<223> OTHER INFORMATION: Synthetic construct
<220> FEATURE:
<221> NAME/KEY: AMIDATION
<222> LOCATION: 10

<400> SEQUENCE: 10

Cys Ala Ala Gln Arg Gln Arg Arg Phe Ile
 1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 10

<400> SEQUENCE: 11

Cys Ala Ala Arg Arg Arg Lys Arg Phe Ile
 1               5                   10

<210> SEQ ID NO 12
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: Arg or Lys
<220> FEATURE:
<221> NAME/KEY: misc_feature
<222> LOCATION: 4
<223> OTHER INFORMATION: Lys or Arg

<400> SEQUENCE: 12

Xaa Arg Gln Xaa Arg Phe
 1               5
```